United States Patent
Angelini et al.

(10) Patent No.: US 6,175,180 B1
(45) Date of Patent: Jan. 16, 2001

(54) METHOD FOR OPTIMIZING THE DRIVE OF A PIEZOELECTRIC ACTUATOR, IN PARTICULAR FOR PHACOEMULSIFIER DEVICES, BY DYNAMIC DETECTION OF ITS ELETROMECHANICAL CHARACTERISTICS AND DEVICES BASED THEREUPON

(75) Inventors: Giov. Battista Angelini; Gualtiero Regini, both of Rome (IT)

(73) Assignee: Optikon 2000 S.p.A. (IT)

( * ) Notice: Under 35 U.S.C. 154(b), the term of this patent shall be extended for 0 days.

(21) Appl. No.: 09/272,516

(22) Filed: Mar. 19, 1999

(30) Foreign Application Priority Data

Mar. 27, 1998 (IT) .............................................. RM98A0202

(51) Int. Cl.[7] ...................................................... B06B 3/00
(52) U.S. Cl. .......................... 310/319; 310/318; 310/338
(58) Field of Search .................................... 310/317, 318, 310/319, 338

(56) References Cited

U.S. PATENT DOCUMENTS

| | | | |
|---|---|---|---|
| 3,903,733 | * 9/1975 | Murayama et al. | 73/659 |
| 4,577,504 | 3/1986 | Kanda et al. | 73/606 |
| 4,952,834 | 8/1990 | Okada | 310/316 |
| 4,986,276 | 1/1991 | Wright | 128/662.04 |
| 5,734,236 | * 3/1998 | Motegi | 310/317 |
| 5,808,396 | * 9/1998 | Boukhay | 310/318 |

FOREIGN PATENT DOCUMENTS

| | | | |
|---|---|---|---|
| 2 219 145 | * 11/1989 | (GB) | 310/318 |

* cited by examiner

Primary Examiner—Thomas M. Dougherty
(74) Attorney, Agent, or Firm—Samuels, Gauthier & Stevens, LLP

(57) ABSTRACT

This invention relates to an optimization method for driving a piezoelectric actuator by dynamic detection of its electromechanical characteristics, as well as to a device, in particular a phacoemulsifier based thereupon. The piezoelectric actuator includes a voltage driven, two-terminal piezoelectric transducer. The method for detection of its electromechanical characteristics is such that the drive of the transducer is cyclically discontinued in order to detect the characteristic parameters of its free motion by detection of the parameters of the signal generated by the transducer at the ends of the two terminals.

11 Claims, 2 Drawing Sheets

Figure 1:
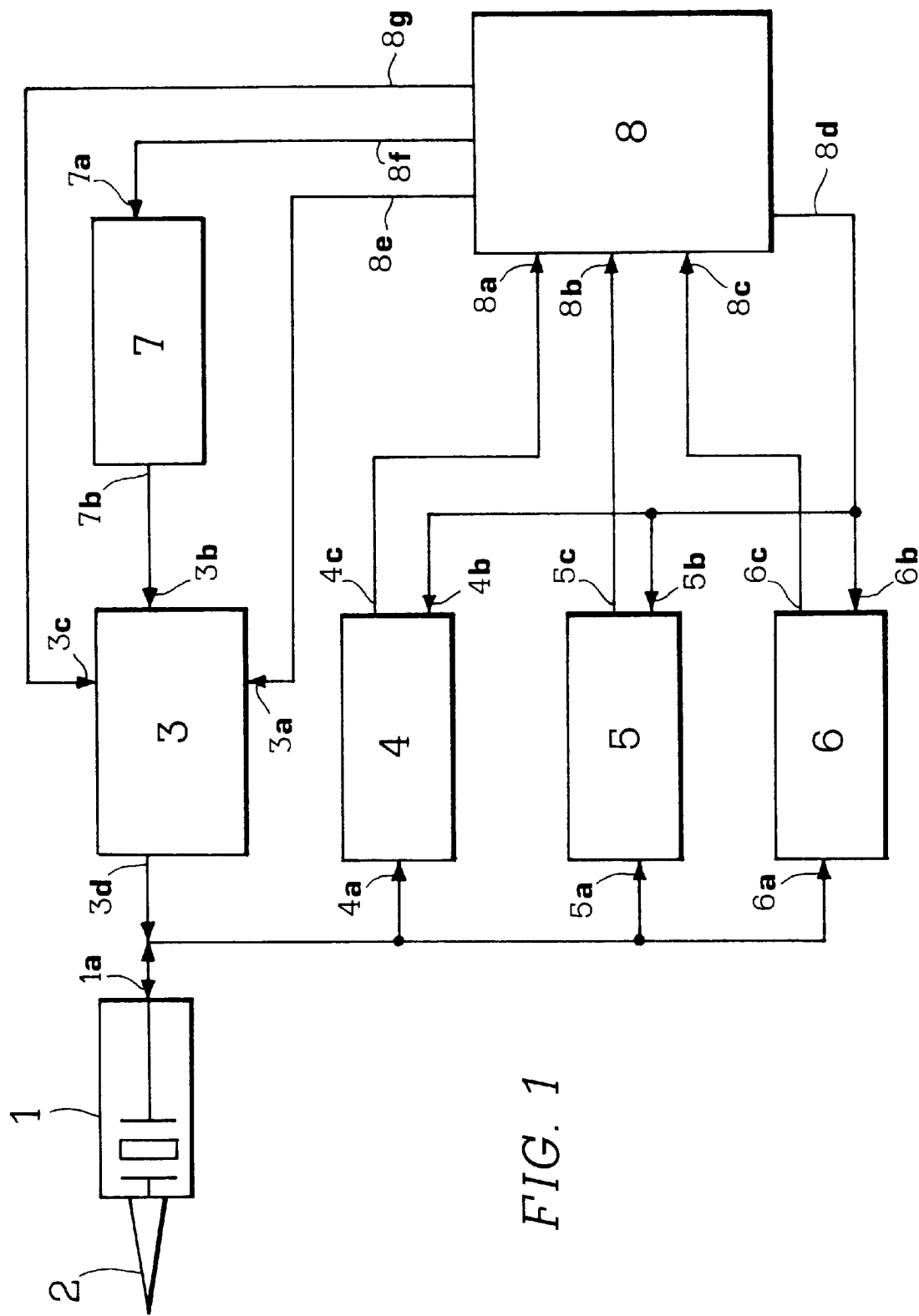

METHOD FOR OPTIMIZING THE DRIVE OF A PIEZOELECTRIC ACTUATOR, IN PARTICULAR FOR PHACOEMULSIFIER DEVICES, BY DYNAMIC DETECTION OF ITS ELETROMECHANICAL CHARACTERISTICS AND DEVICES BASED THEREUPON

This invention broadly relates to a method for controlling a piezoelectric actuator by dynamically detecting its electromechanical characteristics as well as to a device, particularly a phacoemulsifier, including a piezoelectric actuator controlled by means of such method.

More particularly, this invention relates to a method for use in a device including a piezoelectric actuator, which enables to optimize the electric excitation characteristics of said actuator during its operation, thereby assuring the control of the amplitude of its mechanical oscillations and maximizing the efficiency of this device under variable load and environment conditions.

It is known that instruments provided with piezoelectric actuators are extremely popular in various medical-surgical fields. A not exhaustive list of such application fields also includes the ophthalmic surgery, in which said instruments are employed for cataract removal operations; the neurosurgery, for tumor removal operations, as well as odontoiatry.

Only by way of illustration and not by way of limitation, reference will be made in the following description to utilization of such instruments, known under the name of phacoemulsifier devices, in the field of ophthalmic surgery for cataract removal operations.

Cataract removal is one of the most common intervents in the field of ophthalmic surgery and, among the possible techniques for carrying out such intervents, phacoemulsification is becoming more and more popular.

The so-called phacoemulsification technique provides for introducing a needle through a small incision so as to reach the crystalline area and for crumbling the cataract into small pieces, by means of a mechanical action of the needle that oscillates at ultrasonic frequency and with amplitude of some tens micrometers. Such small pieces are subsequently removed from the eye of the patient by means of an aspirator system connected to the same oscillating needle.

The removed material volumes are concurrently replaced by a physiologic salt solution which is delivered through a conduct coaxial to the needle, generally formed by a silicone sleeve arranged outwardly of said needle, which also has the important function to prevent a direct contact between said oscillating needle and the eye tissues, such as the cornea or sclera, thereby preventing the local tissues from being overheated, which could cause necrosis effects thereof.

The conventional phacoemulsifier devices comprise an actuator member comprised of a stack of two or more piezoelectric material ceramics, which are arranged in series relation from a mechanical view point and in parallel relation from an electric view point. Said ceramic stack is mechanically coupled to a pair of metal masses, usually of titanium or steel, one of which, in turn, is coupled to said needle. These ceramic members are excited by a sinusoidal voltage and, by inverse piezoelectric effect, correspondingly modify their own geometries and generate oscillating mechanical strains that are coupled to said pair of metal masses, which, in turn, transmit an oscillating axial displacement to the needle point acting on the concerned cataract.

The system including said ceramics, the pair of metal masses and the needle acts as an oscillator which axially resonates at its own characteristic frequency, determined by the geometry and by the mass of the system. In particular, stationary waves are established in said system and the stationary waves so generated have a point of maximum displacement or "antinode" coincident with the apex of the point and a statical point or "node" coincident with the center point of the ceramic stack.

The circuitry generating the sinusoidal signal for excitation of the system should be adapted to control both the frequency and the amplitude of the excitation signal. In particular, the excitation frequency should always be coincident with the intrinsic mechanical frequency of the system, while the amplitude of the signal determines the power transferred to the system. As a general rule, the amplitude of the excitation signal is adjusted by the surgeon, who trims it based upon the hardness of the concerned cataract as well as on other operatory conditions.

In this respect, all conventional phacoemulsifier devices have various problems due to the difficulties encountered in efficiently controlling the frequency and the amplitude of the excitation signal.

In fact, one of the problems connected with such phacoemulsifier devices is due to the fact that the cataract exerts a load effect on the mechanical system comprising said oscillating needle: when the needle point contacts the cataract, not only the characteristic mechanical frequency of the system varies, but also the oscillation amplitude takes a decreasing behavior and consequently also the emulsifying effect decreases.

As a common practice, aiming at obtaining, during the contact phase between the needle point and the cataract, an oscillation amplitude sufficient to generate in any case the desired emulsifying effect, the excitation generating circuitry transfers a higher power to the involved mechanical system. However, since said circuitry generally does not detect the dynamic variations of the mechanical system, this entails an extremely large oscillation amplitude when the needle point is not in contact relation with the cataract.

Such excessive amplitude oscillation causes a number of drawbacks.

In the first place, cavitation phenomena occur and these phenomena cause, on one hand, the formation of small air bubbles and local boiling actions which noticeably limit the view field of the surgeon. thereby urging him to repeatedly discontinue the emulsifying action on the crystalline for sucking the bubbles themselves and, on the other hand, they reduce the life time of the components of the phacoemulsifier device involved in the cavitation.

In addition, in the case of oscillations of particularly large amplitude, the friction between the oscillating point and the coaxial silicone sleeve can cause such a local overheating as to damage the eye tissues in contact with the sleeve itself.

Lastly, when the oscillation of the mechanical system have excessive large amplitudes, they cause excessively high mechanical stresses on the ceramic components. This, in turn, can cause their breakage or their overheating to temperatures near the Curie depolarization point, thereby degrading their piezoelectric properties.

Various solutions have been studied to minimize the consequences of the mechanical load induced by the cataract on said piezoelectric oscillator and/or to limit the oscillations of the mechanical system when it does not interact with the cataract.

The first solution is a completely mechanical solution and it is based upon utilization of oscillating masses of noticeable dimensions, characterized by a high moment of inertia, so as to be less responsive to the mechanical load furnished by the considered cataract. However, such a solution does not completely solve the problem and besides that it adds further drawbacks. In fact, the increased weight and the large dimensions degrade the manual controllability characteristics of the phacoemulsifier device by the surgeon. In addition, a greater amount of power is needed to maintain these masses in oscillating conditions and, as a consequence of this, greater amounts of heat are generated.

The second solution is based upon measurement of the elongation of the oscillating system during the excitation, by insertion of a displacement sensor and/or an acceleration sensor in the system, such as one or more further piezoelectric ceramics that, upon being pressed by the oscillating masses, generate a signal proportional to the elongation itself, by direct piezoelectric effect. An analog or digital circuitry utilizes such signal in order to produce a feedback signal aimed at controlling the amplitude of the excitation oscillation, so as to stabilize the amplitude of the mechanical oscillation and so make it independent of the applied load. Anyway, also this solution has some drawbacks. First of all, it has the disadvantage that it increases the construction complexity of the phacoemulsifier device and consequently decreases its duration to failure. In the second place, the passive ceramics utilized as sensors act as additional components of the oscillating mechanical system, thereby degrading its efficiency and duration to failure. Due to these drawbacks, the above second solution is not adopted in commercially available phacoemulsifier devices.

A third proposed solution aimed at controlling the oscillations of the concerned mechanical system was disclosed by U.S. Pat. No. 4,223,676. Such solution provides for effecting an indirect detection of the value of the mechanical load acting on the needle point, based upon a measurement of the variation of the resonance frequency of the system induced by the load itself. The latter solution, however, does not appear to be very reliable because the variations of the resonance frequency of the systems are induced not only by the presence of a mechanical load, but also by the changes of the environmental conditions, such as, for instance, an increase of the temperature that causes an expansion of the oscillator.

In this context, the present invention proposes a novel solution that enables the frequency and the amplitude of the excitation signal of a piezoelectric actuator to be effectively controlled so as to contemporaneously solve all above mentioned problems.

It is object of this invention, therefore, to optimize in simple and reliable manner the electric excitation characteristics of a piezoelectric actuator during its operation, besides assuring the control of its mechanical oscillation amplitude and maximizing the efficiency of the device under variable load and environment conditions.

In view of the above, specific subject matter of this invention is a method for optimizing the driving function of a piezoelectric actuator including a piezoelectric transducer, driven by voltage signals, preferably by a sinusoidal signal, more preferably an ultrasonic frequency sinusoidal signal, said piezoelectric transducer having two terminals, said method being characterized in that, for detection of the electromechanical characteristics of the piezoelectric actuator, the driving action of said transducer is cyclically discontinued in order to detect the characteristic parameters of its free motion by detection preferably of the frequency and of the amplitude of the signal generated by said transducer, at the ends of said two terminals.

According to this invention, also the amplitude behavior of the signal generated at the ends of said two terminals can be detected during the interruptions of said driving action.

Again according to this invention, the duration of the interruptions of the driving action can be varied from a minimum time, equal to the sum of the interval extending between the interruption of the driving action and the development of free oscillations of the transducer, and of the period of one single free oscillation cycle, preferably equal to a single sinusoidal cycle, and a maximum time equal to the necessary time for the amplitude of the signal generated at the ends of said two terminals to decrease by 40 dB from the value taken at the begin of the driving action interruption.

Preferably according to the invention, the repetition frequency of said interruptions varies from 2 Hz to 1000 Hz, the driving signal has a frequency equal to 40 kHz and the duration of the interruptions varies from a minimum value of 50 microseconds to a maximum value of 2 milliseconds.

It is a further specific object of this invention to realize a device, preferably a phacoemulsifier device, for carrying out said method, characterized in that it includes a piezoelectric transducer, driven by an alternated voltage, mechanically coupled to a needle and having two terminals as well as electronic components for performing all necessary operations for carrying out said method, as it will be described hereinbelow.

Figure 2:
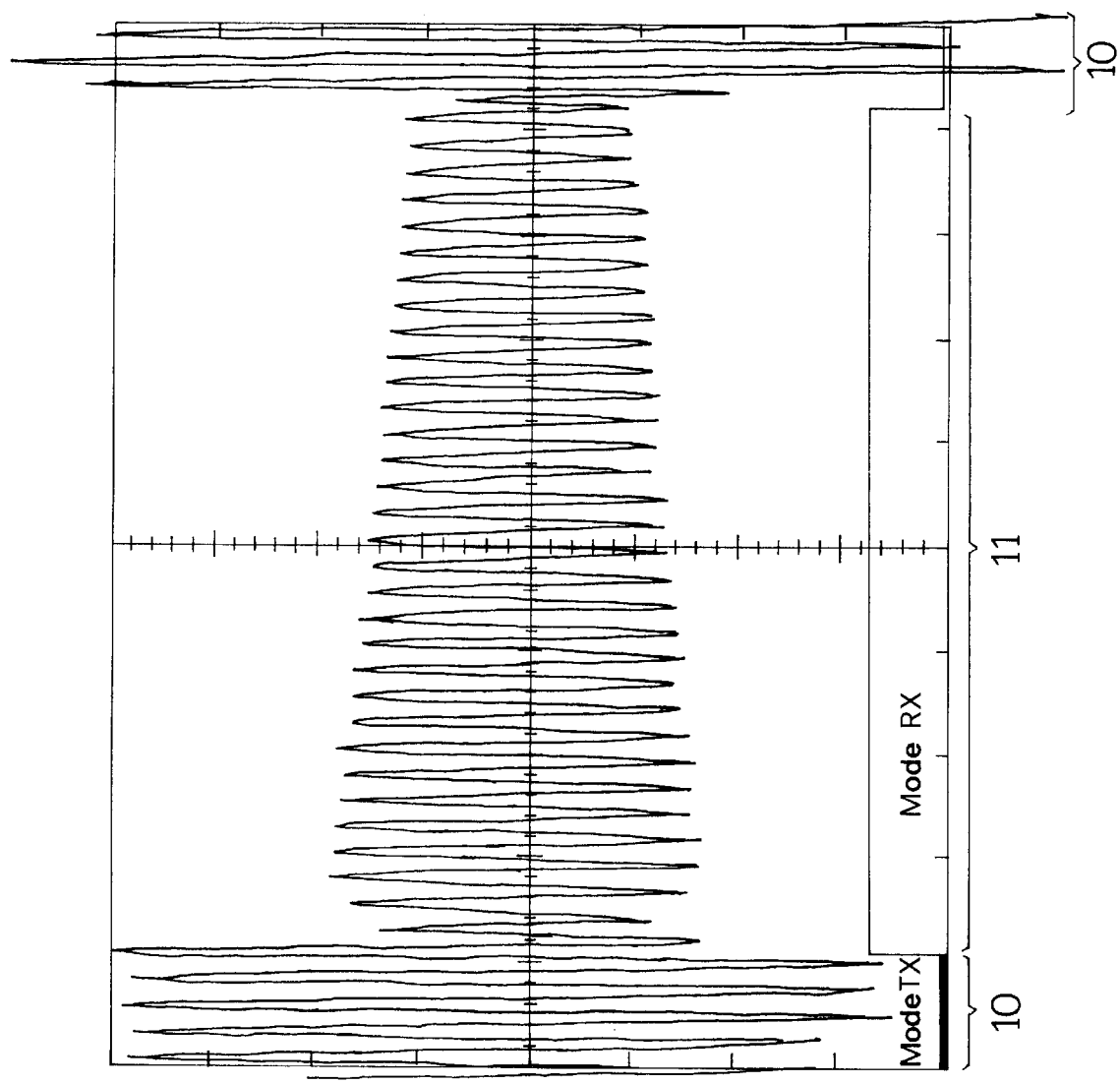

This invention will be now described by way of illustration, but not by way of limitation, in connection with a phacoemulsifier device, according to a preferred embodiment, by particularly referring to the annexed drawing, in which FIG. 1 shows an electronic circuit diagram for controlling and exciting a piezoelectric transducer, acting as an actuator, according to this invention;

FIG. 2 shows the waveform of a voltage signal appearing at the ends of the piezoelectric transducer of FIG. 1.

By referring now to FIG. 1 it can be observed that the handpiece of the phacoemulsifier device according to this invention includes, like all conventional phacoemulsifier devices, a piezoelectric transducer 1 mechanically coupled to a needle 2, by means of a pair of metal masses, not shown, preferably of titanium or steel. Transducer 1, which is voltage driven, has two terminals, one of which can be short-circuited to the circuit ground, designated by reference numeral 1a, and it is made by one or more piezoelectric material ceramics, mechanically arranged in series and electrically arranged in parallel. The mechanical coupling between transducer 1 and needle 2 is such that any deformation of said ceramics produces an axial displacement of said needle 2.

Transducer 1 is connected, by means of said terminals 2a, to an exciter circuit 3, to a power (or amplitude) detector 4, to a frequency detector 5 and to an amplitude behavior detector 6.

Said exciter circuit 3 includes a first input terminal 3a, a second input terminal 3b, a third input terminal 3c and an output terminal 3d, which is connected to terminals 1a of said transducer 1 and can be switched to a high impedance state. In particular, said exciter circuit 3 amplifies, to an amount controlled by signal appearing at said first input terminal 3a, a sinusoidal signal appearing on the second input terminal 3b and furnishes at the output terminal 3d, when it is not in its high impedance state, a sinusoidal signal for driving said transducer 1 acting as an actuator. A suitable signal appearing at said third input terminal 3c presets said output terminal 3d in its high or low impedance state.

A different embodiment of the phacoemulsifier device according to this invention can be implemented so as to include an electronic switching circuit to decouple the exciter circuit 3 from the transducer 1.

The sinusoidal signal appearing on the second input terminal 3b comes from the output terminal 7b of a frequency synthesizer 7. Such synthesizer 7 receives at its input terminal 7a a signal intended for controlling the frequency of the sinusoidal signal to be generated. The accuracy and the stability of said synthesizer depend on the pass band of the piezoelectric transducer 1. In the preferred embodiment of the phacoemulsifier device according to this invention the synthesizer operates at frequencies in the range of 38 kHz to 42 kHz, with a resolution of 10 Hz.

The power detector 4 includes a first input terminal 4a, connected to terminals 1a of transducer 1, a second input terminal 4b and an output terminal 4c. Said detector 4 detects the amplitude of the oscillating voltage signal appearing at the first input terminal 4a and furnishes a corresponding signal representing its value on said output terminal 4c. In particular, a suitable signal on the second input terminal 4b enables or disables such detection.

The frequency detector 5 includes a first input terminal 5a, connected to terminals 1a of transducer 1, a second input terminal 5b and an output terminal 5c. Detector 5 detects the frequency of the oscillating voltage signal appearing on its first input terminal 5a and furnishes a corresponding signal representing it, at the output terminal 5c. In particular, a suitable signal on the second input terminal 5b enables or disables such detection.

The amplitude behavior detector 6 includes a first input terminal 6a, connected to terminals 1a of transducer 1, a second input terminal 6b and an output terminal 6c. Detector 6 detects the behavior of the amplitude, in particular the damping rate, of the oscillating voltage signal appearing on its first input terminal 6a and furnishes a corresponding signal representing it, at the output terminal 6c. In particular, a suitable signal on the second input terminal 6b enables or disables such detection, by determining the time window within which the amplitude behavior of the signal appearing on the first input terminal is considered.

Preferably, the exciter circuit 3, the detectors 4, 5 and 6 and the synthesizer 7 are digitally interfaced, at least as far as the control signals are concerned. Therefore, the signals appearing on the first and third input terminals, 3a and 3c, respectively, of the exciter circuit 3, on the second input terminal 4b and on the output terminal 4c of said detector 4, on the second input terminal 5b and on the output terminal 5c of said detector 5, on the second input terminal 6b and on the output terminal 6c of said detector 6 and on the input terminal 7a of said synthesizer 7 are all digital signals.

The phacoemulsifier device according to the invention additionally includes a control and processing unit 8, consisting of a microprocessor or a digital signal processor (DSP). Said control and processor unit 8 generates all control digital signals to be applied to the above described components and modifies them according to the processing action carried out on the digital signals received from said detectors 4, 5 and 6, in particular, unit 8 includes:

a first input terminal 8a, connected to the output terminal 4c of the power detector 4, a second input terminal 8b, connected to the output terminal 5c of the frequency detector 5, a third input terminal 8c, connected to the output terminal 6c of the amplitude behavior detector 6, a first output terminal 8d, connected to the second input terminal 4b, to the second input terminal 5b and to the second input terminal 6b, respectively, of the power detector 4, of the frequency detector 5 and of the amplitude behavior detector 6, a second output terminal 8e, connected to the first input terminal of the exciter circuit 3, a third output terminal 8f, connected to the input terminal 7a of said synthesizer 7, and a fourth output terminal 8g, connected to the third input terminal 3c of the exciter circuit 3 (in particular, the signal appearing on the fourth output terminal 8g can be coincident with the signal appearing on the first output terminal 8d).

The phacoemulsifier device according to the invention allows to measure the oscillation amplitude., the mechanical resonance frequency and the efficiency of the piezoelectric transducer 1, operating as an actuator that furnishes motive power to the needle 2, during its operation and in all mechanical load conditions, by utilization of said piezoelectric transducer 1 as a detector of the electromechanical characteristics of the system comprised of the transducer 1 itself, of the needle 2 and also by the mechanical load induced by the cataract. Said control and processing unit 8 is programmed for carrying out the method of the present invention, according to which said transducer 1 exclusively operates as an actuator, in a first operation phase designated as transmission mode or mode TX, or exclusively as a sensor in a second operation phase designated as a reception mode or mode RX.

During mode TX, said unit 8 transmits suitable signals to said exciter circuit 3 and to said synthesizer 7 in order to let the exciter circuit 3 furnish a driving voltage at ultrasonic frequency to said piezoelectric transducer 1, sufficient to drive said piezoelectric ceramics into oscillation by inverse piezoelectric effect.

Said unit 8, by modifying the signal appearing on the fourth output terminal 8g, cyclically switches the exciter circuit 3 with its output terminal 3d to the high impedance state, thereby interrupting consequently the driving voltage of the transducer 1 which switches to the operation mode RX.

During operation in mode RX, the mechanical system comprised of transducer 1, needle 2 and possibly the mechanical load induced by the concerned cataract continues freely oscillating at its own characteristic frequency. The oscillations of said transducer 1 generate at the ends of terminals 1a, by direct piezoelectric effect, a voltage having a frequency equal to the free resonance frequency of the mechanical system and an amplitude proportional to the amplitude of the mechanical oscillations. Therefore, during operation in mode RX, said transducer 1 operates as a sensor. It will be apparent to those skilled in the art that said oscillating voltage appearing at the ends of terminals 1a has an amplitude which is decreasing as a function of the time.

During operation in mode RX, the oscillating voltage signal appearing at the ends of terminals 1a is analyzed by detectors 4, 5 and 6, suitably enabled by the signal coming from the first output terminal 8d of unit 8. In particular, detectors 4 and 5 detect the amplitude and the frequency of said signal, while detector 6 measures the amplitude decay of the damped free oscillations of the mechanical system comprised of the transducer 1, of the needle 2 and possibly of the mechanical load induced by the cataract, thereby furnishing a measure of the efficiency of the whole system. At the end of the time period in which said transducer operates in mode RX, said unit 8 suitably modifies the signal appearing on the first output terminal 8d and all information relating to the amplitude or to the power and to the frequency of the signal, as well as to the efficiency of the above mentioned mechanical system is transmitted to said detectors 4, 5 and 6, respectively, to the first input terminal 8a, to the second input terminal 8b and to the third input terminal 8c of said unit 8.

Unit 8 processes the received information so as to set the frequency of the excitation signal of said transducer 1 by modifying the signal applied to the third output terminal 8f in order to drive the handpiece at the correct resonance frequency, so as to optimize its performances as well as its efficiency, and to stabilize the amplitude of the oscillations as a function of the mechanical load of the handpiece, by suitably varying the amplitude of the driving sinusoidal signal by means of a corresponding variation of the signal transmitted to the second output terminal 8e. Furthermore, said unit 8 stabilizes the displacement amplitude of the needle 2 of the handpiece, thereby also resisting the middle and long term variations of the handpiece characteristics.

At the end of the time period in which the transducer operates in mode RX, said unit 8 modifies the signal appearing on the fourth output terminal 8g in order to drive said piezoelectric transducer 1 so as to operate again in mode TX as an actuator.

As it will be described hereinbelow, the duration of operation mode RX is preferably negligible with respect to the repetition period of the interruptions, in order not to significantly decrease the power furnished to transducer 1.

The phacoemulsifier device according to this invention can be arranged so that detector 4 can detect the amplitude of the signal applied to the transducer 1 also during operation in mode TX and that the related information can be communicated to unit 8. Since transducer 1 utilized as a sensor in mode RX is the same transducer 1 utilized as an actuator in mode TX, the ratio $V_{RX}/V_{TX}$ between the amplitude $V_{RX}$ of the voltage signal generated by the free oscillations of the system, measured in mode RX, and the amplitude $V_{TX}$ of the voltage signal utilized to excite the transducer 1, measured in mode TX, can be processed by unit 8 in order to obtain an evaluation of the efficiency of the system, thereby supporting the data obtained by said detector 6 or wholly eliminating said detector 6.

Similarly, the phacoemulsifier device according to this invention can be arranged so that detector 5 can detect the frequency of the signal applied to the transducer 1 also during operation in mode TX and that the related information can be communicated to unit 8. In particular, if the above mentioned synthesizer 7 is of a frequency locked type, the measured frequency value of the drive signal can be utilized for controlling the synthesizer itself.

In addition, the control and process unit 8 can determine any degradation condition of the electromechanical efficiency or any failure in the handpiece, by evaluating the ratio between the measured voltage and the applied voltage and/or by analyzing the decay of the free oscillations of said transducer 1 in not excited condition, and/or it can recognize abnormal use conditions of the handpiece, such as its operation in the air, by signalling them and/or by limiting them and/or by preventing them.

By referring now to FIG. 2, it is possible to observe the waveform of the voltage signal appearing at the terminals of the piezoelectric transducer 1 of FIG. 1 during the two operation phases in mode RX and in mode TX. In particular, the waveform relating to mode TX is designated by reference numeral 10, while the waveform relating to mode RX is designated by reference numeral 11.

The minimum duration in operation mode RX should allow for the completion of the switching transition interval, which could amount to one oscillation period of said transducer 1 excited at an ultrasonic frequency, as well as for the detection of at least two cycles of the damped oscillation. The maximum duration of the operation mode RX depends on the construction characteristics of the handpiece and it should not overcome the necessary time for the amplitude of the signal appearing at the ends of terminals 1a, as generated by free oscillations of the mechanical system, to decay to values lower than the minimum value that detectors 4, 5 and 6 can detect. As a matter of fact, the whole decay range up to −40 dB of the initial value can be useful for the control system. By way of illustration, when the excitation frequency is equal to 40 kHz, the duration of the operation in mode RX can advantageously vary from 1 to 80 free oscillation periods of transducer 1, corresponding to an interval of 25 to 2000 microseconds.

Preferably, the duration of operation in mode RX is of negligible length with respect to the repetition period of the interruptions, so as not to significantly reduce the power supplied to the oscillator. In particular, the repetition frequency of the operation phase in mode RX can be in the range of 2 to 1000 Hz, depending on the specific application.

It is apparent to those skilled in the art that the repetition period as well as the duration of the interruptions (mode RX) can be determined according to the requirements connected with the response speed of the control system.

The handpiece comprising said transducer 1 can also include in it or within the insertion connector utilized for connection with said phacoemulsifier device, a non-volatile memory device, such as a nonvolatile electronically programmable and erasable memory device (EEPROM: Electronically Erasable Programmable Read-Only Memory), which is accessed in write and read operations by said control and processing unit 8. Said memory device is adapted to store a series of data characterizing the electromechanical properties of the handpiece as well as of the handpiece control and excitation electronic circuit.

In particular, said memory device can be programmed during its testing procedure so as to store the original value of the $V_{RX}/V_{TX}$ ratio between the amplitude $V_{RX}$ of the signal measured at the ends of terminals 1a in operation mode RX and the amplitude $V_{TX}$ of the signal measured at the ends of terminals 1a in operation mode TX for a pre-established reference elongation $E_o$. Such original value can be utilized by unit 8 during the operation life of the phacoemulsifier device in order to check the constancy of the $V_{RX}/V_{TX}$ ratio and for indicating the need to maintain or to substitute the concerned handpiece when the deviation of said ratio from the value measured during the manufacturing stage is higher than a threshold amount.

The above said memory device can also be programmed for storing the proportionality constant $K_o$ between a certain reference elongation $E_o$ and the corresponding amplitude $V_{RX}$ of the signal measured in operation mode RX. In particular, it is well known to those skilled in the art that such proportionality constant $K_o$ takes different values in different handpieces, because it is a function of many construction variables. Based upon reading the proportionality constant $K_o$ stored in said memory device, unit 8 enables the surgeon to directly set the amplitude of the oscillations of the needle 2 in micrometer units.

Said memory device can also be programmed by said unit 8 at the end of each operation of the handpiece in order to store the effective cumulative utilization time of the handpiece itself. In such case, unit 8 could also indicate the need of periodic maintenance intervents or the substitution of the concerned handpiece.

According to the preferred embodiment of the device of this invention, the electronic circuit for controlling and exciting the piezoelectric transducer 1 can also be implemented in digital technology. It should be understood, however, that said circuit can also be wholly realized with analog components, without departing from the coverage of this invention.

Furthermore, the device according to this invention has been described with particular reference to phacoemulsifier devices. It should be understood that the abovesaid device can also be any device comprising a piezoelectric actuator, without so departing from the scope of the present invention.

The preferred embodiments of this invention have been described and a number of variations have been suggested hereinbefore, but it should expressly be understood that those skilled in the art can make other variations and changes, without so departing from the scope thereof, as defined in the annexed claims.

What is claimed is:

1. An optimization method for driving a piezoelectric actuator by dynamic detection of its electromechanical characteristics, the piezoelectric actuator including a voltage driven, two-terminal piezoelectric transducer, said method for detection of the electromechanical characteristics of the piezoelectric actuator comprising, the drive of said transducer being cyclically interrupted in order to detect the characteristic parameters of its free motion by detection of the parameters of the signal generated by said transducer at the ends of said two terminals.

2. The method according to claim 1, wherein said transducer is driven by a sinusoidal signal and in that the characteristic parameters of the free oscillations of said transducer are detected during the interruptions of the driving action by detecting the frequency and the amplitude of the signal generated at the ends of said two terminals.

3. The method according to claim 2, wherein the amplitude behavior of the signal generated at the ends of said two terminals is detected during the interruptions of said driving action.

4. The method according to claim 2, wherein the duration of the interruptions of the driving action varied from a minimum time, equal to the sum of the interval extending between the interruption of the driving action and the development of free oscillations of the transducer, and of the period of one single free oscillation cycle, and a maximum time equal to the necessary time for the amplitude of the signal generated at the ends of said two terminals to decrease by 40 dB from the value taken at the beginning of the driving action interruption.

5. The method according to claim 2, wherein the excitation sinusoidal signal has an ultrasonic frequency.

6. The method according to claim 5, wherein the repetition frequency of the interruptions varies in the range of 2 Hz to 1000 Hz.

7. The method according to claim 6, wherein the driving sinusoidal signal has a frequency of 40 kHz and the duration of the interruptions varies from a minimum value of 50 microseconds to a maximum value of 2 milliseconds.

8. A device for performing the method according to claim 2, wherein it includes a piezoelectric transducer, driven by voltage signals and having two terminals, an exciter circuit, an amplitude detector, a frequency detector, a frequency synthesizer and a control and processing unit, said transducer being realized by one or more piezoelectric material ceramics, arranged in series relation from a mechanical view point and in parallel relation from an electrical view point; said transducer being also connected, by means of said terminals, to said exciter circuit, to said amplitude detector and to said frequency detector; said exciter circuit amplifying a sinusoidal signal coming from said synthesizer; said control and processing unit including a microprocessor or a digital signal processor (DSP) and receiving the signal corresponding to the detections carried out by said amplitude detector and by said frequency detector; said control and processing unit generating a control signal for controlling said exciter circuit, a signal for enabling the connection between said exciter circuit and the transducer, a signal for controlling the frequency of the synthesizer, a signal for enabling the operation of said amplitude detector and a signal for enabling the operation of said frequency detector.

9. The device according to claim 8, wherein said transducer is included in a handpiece which further comprises a non-volatile memory device which is accessed in read and write operations by said control and processing unit.

10. The device according to claim 8, wherein it also includes an amplitude behavior detector connected to said transducer by means of said terminals, in that said control and processing unit receives the signal corresponding to the detection of the amplitude behavior performed by said amplitude behavior detector and generates a signal for enabling the detection of the amplitude behavior by said amplitude behavior detector.

11. The device according to claim 8, wherein it is a phacoemulsifier device and said piezoelectric transducer is mechanically coupled, by means of a pair of metal masses, preferably of titanium or steel, to a needle, such mechanical coupling being such that any deformation of said transducer generates an axial displacement of said needle.

* * * * *